US011654028B2

United States Patent
Souza et al.

(10) Patent No.: US 11,654,028 B2
(45) Date of Patent: May 23, 2023

(54) IMPLANTS AND TECHNIQUES FOR TISSUE FIXATION AND FUSION

(71) Applicant: CUTTING EDGE SPINE LLC, Waxhaw, NC (US)

(72) Inventors: John Souza, Wesley Chapel, NC (US); Kyle Kuntz, Waxhaw, NC (US)

(73) Assignee: CUTTING EDGE SPINE LLC, Waxhaw, NC (US)

( * ) Notice: Subject to any disclaimer, the term of this patent is extended or adjusted under 35 U.S.C. 154(b) by 449 days.

(21) Appl. No.: 16/799,002

(22) Filed: Feb. 24, 2020

(65) Prior Publication Data

US 2020/0222189 A1 Jul. 16, 2020

Related U.S. Application Data

(62) Division of application No. 15/487,292, filed on Apr. 13, 2017, now Pat. No. 10,588,750.

(60) Provisional application No. 62/322,435, filed on Apr. 14, 2016.

(51) Int. Cl.
| | |
|---|---|
| *A61B 17/86* | (2006.01) |
| *A61F 2/44* | (2006.01) |
| *A61F 2/30* | (2006.01) |
| *A61B 17/68* | (2006.01) |

(Continued)

(52) U.S. Cl.
CPC ............. *A61F 2/30* (2013.01); *A61B 17/68* (2013.01); *A61B 17/7055* (2013.01); *A61B 17/8685* (2013.01); *A61F 2/28* (2013.01); *A61B 17/8695* (2013.01); *A61F 2/30767* (2013.01);

(Continued)

(58) Field of Classification Search
CPC ...................................... A61B 17/86–17/8695
See application file for complete search history.

(56) References Cited

U.S. PATENT DOCUMENTS

| 645,139 | A | * | 3/1900 | Sloan | B23G 1/22 |
|---|---|---|---|---|---|
| | | | | | 470/58 |
| 2,083,766 | A | * | 6/1937 | Wittkopp | B60C 7/24 |
| | | | | | 152/394 |

(Continued)

FOREIGN PATENT DOCUMENTS

WO 2002034120 A2 5/2002

OTHER PUBLICATIONS

Zimmer Product Brochure, "Zimmer Trabecular Metal Dental Implant," 8 pgs., 2012.

(Continued)

*Primary Examiner* — Zade Coley
(74) *Attorney, Agent, or Firm* — McNees Wallace & Nurick LLC

(57) ABSTRACT

A tissue fixation implant that includes leading fixation and trailing fixation members, each fixation member having a proximal head and an elongate shank with a distal tip, and each fixation member adapted to at least partially contact the other fixation member at one or more points along their respective lengths. The tissue fixation implant includes a proximal inter-engagement feature for fixedly engaging each of the two fixation members relative to one another when engaged within tissue, including bone tissue, soft tissue, and combinations of these, and has an interior chamber suitable for receiving osteogenic material to enhance new bone growth and fusion of the fixation implant within bone.

3 Claims, 10 Drawing Sheets

(51) Int. Cl.
*A61B 17/70* (2006.01)
*A61F 2/28* (2006.01)

(52) U.S. Cl.
CPC .............. *A61F 2002/30593* (2013.01); *A61F 2002/30995* (2013.01); *A61F 2220/0008* (2013.01)

(56) References Cited

U.S. PATENT DOCUMENTS

| | | | | |
|---|---|---|---|---|
| 3,474,537 | A * | 10/1969 | Christensen | A61C 8/0009 433/174 |
| 5,417,692 | A | 5/1995 | Goble et al. | |
| D359,557 | S | 6/1995 | Hayes | |
| 5,984,681 | A * | 11/1999 | Huang | A61C 8/0009 433/173 |
| 6,485,517 | B1 * | 11/2002 | Michelson | A61F 2/447 623/17.11 |
| 6,572,315 | B1 * | 6/2003 | Reed | F16B 39/30 411/411 |
| 6,960,216 | B2 | 11/2005 | Kolb et al. | |
| 7,011,659 | B2 * | 3/2006 | Lewis | A61B 17/7056 606/276 |
| 7,534,265 | B1 * | 5/2009 | Boyd | A61F 2/28 623/17.11 |
| 7,736,381 | B2 | 6/2010 | Biedermann et al. | |
| 8,231,387 | B2 | 7/2012 | Salvi et al. | |
| 8,343,220 | B2 * | 1/2013 | Michelson | A61F 2/446 623/17.11 |
| 8,989,911 | B2 | 3/2015 | Martineau et al. | |
| 2004/0133207 | A1 * | 7/2004 | Abdou | A61B 17/7059 606/279 |
| 2005/0149024 | A1 * | 7/2005 | Ferrante | A61B 17/746 606/62 |
| 2006/0036244 | A1 * | 2/2006 | Spitler | A61B 17/1604 606/328 |
| 2006/0116679 | A1 | 6/2006 | Lutz et al. | |
| 2007/0162019 | A1 | 7/2007 | Burns et al. | |
| 2009/0254126 | A1 | 10/2009 | Orbay et al. | |
| 2009/0259261 | A1 | 10/2009 | Reiley | |
| 2010/0036498 | A1 * | 2/2010 | McDevitt | A61F 2/446 606/246 |
| 2011/0208252 | A1 * | 8/2011 | Erhart | A61B 17/1735 606/310 |
| 2011/0270325 | A1 * | 11/2011 | Keyer | A61B 17/7037 606/305 |
| 2013/0245763 | A1 | 9/2013 | Mauldin | |
| 2014/0052255 | A1 * | 2/2014 | DeFalco | A61B 17/8057 606/286 |
| 2016/0157908 | A1 | 6/2016 | Cawley et al. | |

OTHER PUBLICATIONS

Search Report issued to PCT counterpart application No. PCT/US2017/027481 by the International Searching Authority dated Aug. 31, 2017.

* cited by examiner

IMPLANTS AND TECHNIQUES FOR TISSUE FIXATION AND FUSION

RELATED APPLICATIONS

This application is a divisional of U.S. patent application Ser. No. 15/487,292 entitled IMPLANTS AND TECHNIQUES FOR TISSUE FIXATION AND FUSION filed on Apr. 13, 2017, and claims the benefit of U.S. Provisional Patent Application Ser. No. 62/322,435 entitled ORTHOPEDIC SCREWS filed on Apr. 14, 2016, the entirety of which applications are incorporated by reference herein

FIELD

The present application describes various exemplary devices and surgical techniques for securing tissue, particularly bone tissue in the spine, and more particularly, associated with the sacroiliac joint.

DESCRIPTION OF THE RELATED ART

A variety of orthopedic conditions, including injuries, degeneration, and congenital abnormalities can present the need for interventional implants and surgical techniques to achieve one or more of bone repair, stabilization, and correction. Conventional procedures have been developed using mechanical implants, for example to straighten or otherwise stabilize joints, secure fragments of fractured bones, and secure and stabilize successive vertebrae, sacral iliac bones, and other adjacent bones in a fixed position. These implants include bone screws, anchors, rods, bands, plates, and combinations of these devices that are comprised of one or a combination of metal, polymers, biomaterials and other biologically acceptable materials.

In one example, fixation and fusion is needed for addressing sacroiliac dysfunction or instability that occurs in the sacroiliac joint. In a typical subject, the sacroiliac joint spans between the sacrum bone and ilium bone, and has a natural degree or motion, or nutation, of one to two degrees. In the case of injury to the joint, the typically small range of motion can be exaggerated and lead to hypermobility, an often difficult condition to diagnose because it involves lower back and leg pain which are symptoms that are common with other spinal and orthopedic problems. Once diagnosed, there are surgical options for fixation and fusion of the sacroiliac joint. But due to the natural movement of the joint, typical bone screw type implants can be vulnerable to rotation and ultimate failure.

Accordingly, there is a need for implant devices that can correct sacroiliac instability and hypermobility with resistance to rotational and pull out failures in order to achieve the desirable degree of fusion across the joint. Such improved devices are needed for the maintenance of stability of securement of the bones, for example prevention of rotation of one or both of bone and implant that can destabilize fixation and cause movement or migration of the joined bone, of the implant, and combinations of these. In some particular applications, there is a need for devices that enhance and provide more secure fixations of the sacroiliac joint, including greater bone purchase and retention, and features for enhanced tissue integration.

SUMMARY

In accordance with various embodiments, the invention provides a fixation implant that comprises a leading fixation member and a trailing fixation member, each such fixation member having a proximal head and an elongate shank with a distal tip, and each fixation member is adapted to at least partially contact the other fixation member at one or more points along their respective lengths. The tissue fixation implant includes an inter-engagement feature for fixedly engaging each of the two fixation members relative to one another when engaged within tissue, including bone tissue, soft tissue, and combinations of these.

The fixation implant is advantageously used for accomplishing fixation of tissue, such as bone tissue, in some examples including adjacent bones at a joint such as the sacroiliac joint, or bone fracture fragments. The implant provides enhanced resistance to rotational motion, rotational migration and pull out as compared with unitary fixation member designs, this advantage owing to one or more of the increased bone engagement surface, enhanced opportunity for osseo-integration, resistance to rotation, and enhanced bone purchase at the distal end of the implant. The fixation implant can include fixation members having features that are selected from one of a conventional threaded bone screw, such as a SI screw, a non-threaded press fit plug, and other embodiments of bone fixation screws known in the art.

BRIEF DESCRIPTION OF THE DRAWINGS

Features and advantages of the general inventive concepts will become apparent from the following description made with reference to the accompanying drawings, including drawings represented herein in the attached set of figures, of which the following is a brief description.

Figure 1:
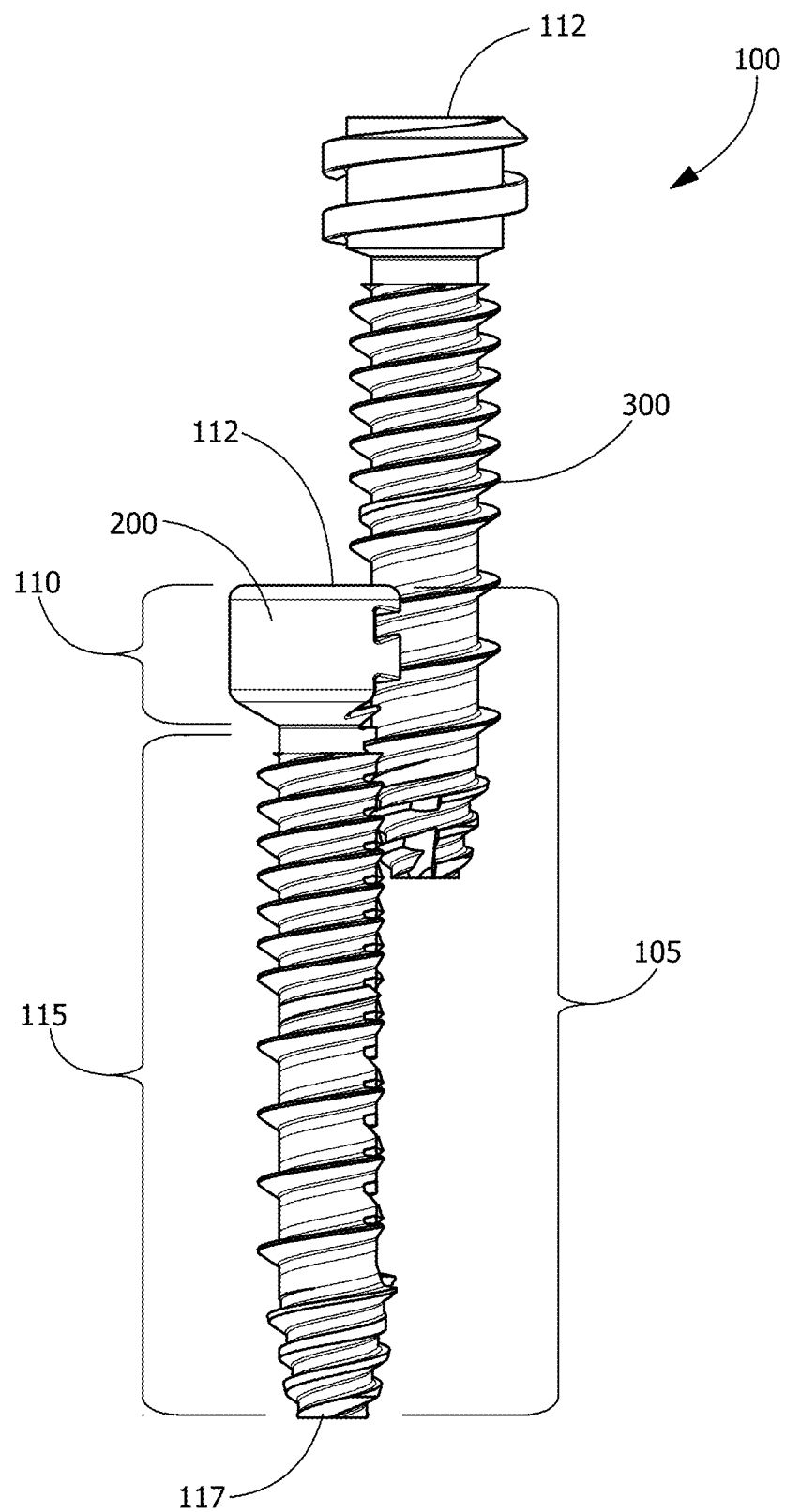
FIG. 1 shows one embodiment of a fixation implant that includes a pair of bone fixation members in a partially engaged configuration.

This disclosure describes exemplary embodiments in accordance with the general inventive concepts and is not intended to limit the scope of the invention in any way. Indeed, the invention as described in the specification is broader than and unlimited by the exemplary embodiments set forth herein, and the terms used herein have their full ordinary meaning.

DETAILED DESCRIPTION

The general inventive concepts will now be described with occasional reference to the exemplary embodiments of the invention. The general inventive concepts may be embodied in different forms and should not be construed as limited to the embodiments set forth herein. Rather, these embodiments are provided so that this disclosure will be thorough and complete, and will fully convey the scope of the general inventive concepts to those skilled in the art.

As used herein, the singular forms "a," "an," and "the" are intended to include the plural forms as well, unless the context clearly indicates otherwise. The term "proximal" as used in connection with any object refers to the portion of the object that is closest to the operator of the object (or some other stated reference point), and the term "distal" refers to the portion of the object that is farthest from the operator of the object (or some other stated reference point). The term "operator" means and refers to any professional or paraprofessional who delivers clinical care to a medical patient, particularly in connection with the delivery of care.

Anatomical references as used herein are intended to have the standard meaning for such terms as understood in the medical community, and generally, any and all terms providing spatial references to anatomical features shall have meaning that is customary in the art. For example, the application may include reference to the following terms: "cephalad," "cranial" and "superior" indicate a direction toward the head, and the terms "caudad" and "inferior" indicate a direction toward the feet. Likewise, the terms "dorsal" and "posterior" indicate a direction toward the back, and the terms "ventral" and "anterior" indicate a direction toward the front. And the term "lateral" indicates a direction toward a side of the patient. The term "medial" indicates a direction toward the mid line of the patient, and away from the side, the term "ipsalateral" indicates a direction toward a side that is proximal to the operator or the object being referenced, and the term "contralateral" indicates a direction toward a side that is distal to the operator or the object being referenced.

"Patient" is used to describe an animal, preferably a human, to whom treatment is administered, including prophylactic treatment with the compositions of the present invention. "Concave" is used herein to describe an indented surface without reference to the specific shape of the indented surface. As non-limiting examples, the concave face may be tubular with a round cross section, oval cross section, square cross section, or rectangular cross section.

Unless otherwise indicated, all numbers expressing quantities, properties, and so forth as used in the specification, drawings and claims are to be understood as being modified in all instances by the term "about." Accordingly, unless otherwise indicated, the numerical properties set forth in the specification and claims are approximations that may vary depending on the suitable properties desired in embodiments of the present invention. Notwithstanding that the numerical ranges and parameters setting forth the broad scope of the general inventive concepts are approximations, the numerical values set forth in the specific examples are reported as precisely as possible. Any numerical values, however, inherently contain certain errors necessarily resulting from error found in their respective measurements.

References to visualization using radiography as may be described in the exemplary techniques herein are merely representative of the options for the operator to visualize the surgical field and the patient in one of many available modalities. It will be understood by one of ordinary skill in the art that alternate devices and alternate modalities of visualization may be employed depending on the availability in the operating room, the preferences of the operator and other factors relating to exposure limits. While confirmation of instrument placement in the course of the technique is appropriate, the frequency and timing relative to the sequence of steps in the technique may be varied and the description herein is not intended to be limiting. Accordingly, more or fewer images, from more or fewer perspectives, may be collected.

One of ordinary skill will appreciate that references to positions in the body are merely representative for a particular surgical approach. Further, some references herein are made in the context of the representative images shown in the drawings. Fewer or additional instruments, including generic instruments, may be used according to the preference of the operator. Moreover, references herein to specific instruments are not intended to be limiting in terms of the options for use of other instruments where generic options are available, or according to the preference of the operator.

Fixation Implants

The present application describes various embodiments of devices for joint and other bone fixation. In some particular embodiments, devices for fixation of the sacroiliac joint are provided. It will be appreciated that the examples and drawings, as shown herein, may be described in reference to use in applications for sacroiliac joint fusion, though the devices as disclosed herein may be used in any of a variety of other orthopedic applications, and may be used alone, or as an adjunct to devices used for other fixation or correction, such as, for example, in spine fusion surgery, to help hold other implants in place.

In accordance with various embodiments, the invention provides a fixation implant that comprises a leading fixation member and a trailing fixation member, each such fixation member having a proximal head and an elongate shank with a distal tip, and each fixation member is adapted to at least partially contact the other fixation member at one or more points along their respective lengths. The tissue fixation implant includes an inter-engagement feature for fixedly engaging each of the two fixation members relative to one another when engaged within tissue, including bone tissue, soft tissue, and combinations of these.

In accordance with the various embodiments, the fixation implant has an interior chamber defined by the leading and trailing fixation members, the chamber suitable for receiving osteogenic material to enhance new bone growth and fusion of the fixation implant within bone. In some embodiments, the shank of at least one of the fixation members includes one or more openings or slots through the elongate shank, in some embodiments arranged as a plurality around the periphery of the shank, to further enhance bony ingrowth.

The fixation implant is advantageously used for accomplishing fixation of tissue, such as bone tissue, in some examples including adjacent bones at a joint such as the sacroiliac joint, or bone fracture fragments. The implant provides enhanced resistance to rotational motion, rotational migration and pull out as compared with unitary fixation member designs, this advantage owing to one or more of the increased bone engagement surface, enhanced opportunity for osseo-integration, resistance to rotation, and enhanced bone purchase at the distal end of the implant. The fixation implant can include fixation members having features that are selected from one of a conventional threaded bone screw, such as a SI screw, a non-threaded press fit plug, and other embodiments of bone fixation screws.

In some representative embodiments, one or both of the fixation members of the fixation implant is or resembles a bone screw, insofar as such fixation member includes a head and an elongated body that includes a threaded portion arranged in a spiral pattern (helical) around the circumference and along at least a portion of a length of the fixation member, and in some embodiments, a shank portion that is proximate to the head that is not threaded. It will be appreciated that such fixation members may comprise one or more different thread features that may vary in any one or more of frequency, pitch, helix angle, thread angle, and major and minor diameters, and the threading may be male (extending away from the body of the shank), female (notches, grooves or channels cut into the body of the shank for receiving male threads), and combinations of these. Further, any one or more of the thread features may be shaped as known in the art, including shapes selected from V-, square-, buttress-, reverse buttress threaded, and combinations of these, and the thread features may be left or right hand oriented, and the thread features may be self-cutting or self-tapping, or non-self-cutting or non-self-tapping, and combinations of these. As described variously herein, a fixation member having external threading may alternately be referred to as a screw.

In yet other representative embodiments, one or both of the fixation members of the fixation implant is or resembles a bone anchor or plug insofar as such fixation member includes a head and an elongated body that is not threaded. It will be appreciated that in some such embodiments, such fixation members may comprise one or more surface features for enhancing engagement with tissue such as cortical or cancellous bone, such features including but not limited to, keels, fins, and distal bulbs or protuberances.

In accordance with the various embodiments, at least one of the fixation members has an overall cylindrical, conical, or frusto conical shape that has either a fixed or an increasing diameter from distal to proximal. It will be appreciated that in some embodiments, at least one of the fixation members may lack one or both of a distal threaded portion and a proximal head, and as such may have an overall cylindrical, conical, or frusto conical shape that has a fixed or an increasing diameter from distal to proximal and may be devoid of any threading or head features. In some specific embodiments, the head has a frusto conical or a spherical or hemispherical shape. And in some embodiments, the elongate shank has an overall or generally cylindrical shape, with a tapered or conical distal tip. In various embodiments, the fixation members may have elongate shanks that are fully threaded, or that have a short unthreaded portion, or that are entirely unthreaded.

In some embodiments a fixation member has a head with a flat surface or top and an enlarged outer diameter relative to the outer diameter of the elongate shank, wherein the head may include an internal bore with one or more internal engagement features for receiving a driver. Such features may include one or a hex configuration for receiving a hex driver, or internal threading for receiving a threaded driver cap, or any of a variety of other possible engagement features. The head and elongate shank of the fixation member, and any threaded driver cap is, in some embodiments, cannulated for receiving a guide, or k-wire there through.

Also in accordance with the disclosure are techniques that are generally characterized as including the steps of placing a guide wire or a k-wire at an insertion site for the implant, inserting a fixation member over the wire, inserting a cannulated drill guide over the guide wire and using a cannulated drill to pre-drill a pilot hole, and then inserting the screw onto the guide wire to direct the path for insertion into the bone, then using a cannulated driver or other appropriate tool to drive the implant into the bone to traverse the joint and thereby join the sacrum and the ilium. It will be appreciated that in some embodiments, one or more of the fixation members may not be cannulated, thus the steps of implantation may vary accordingly.

Figure 10:
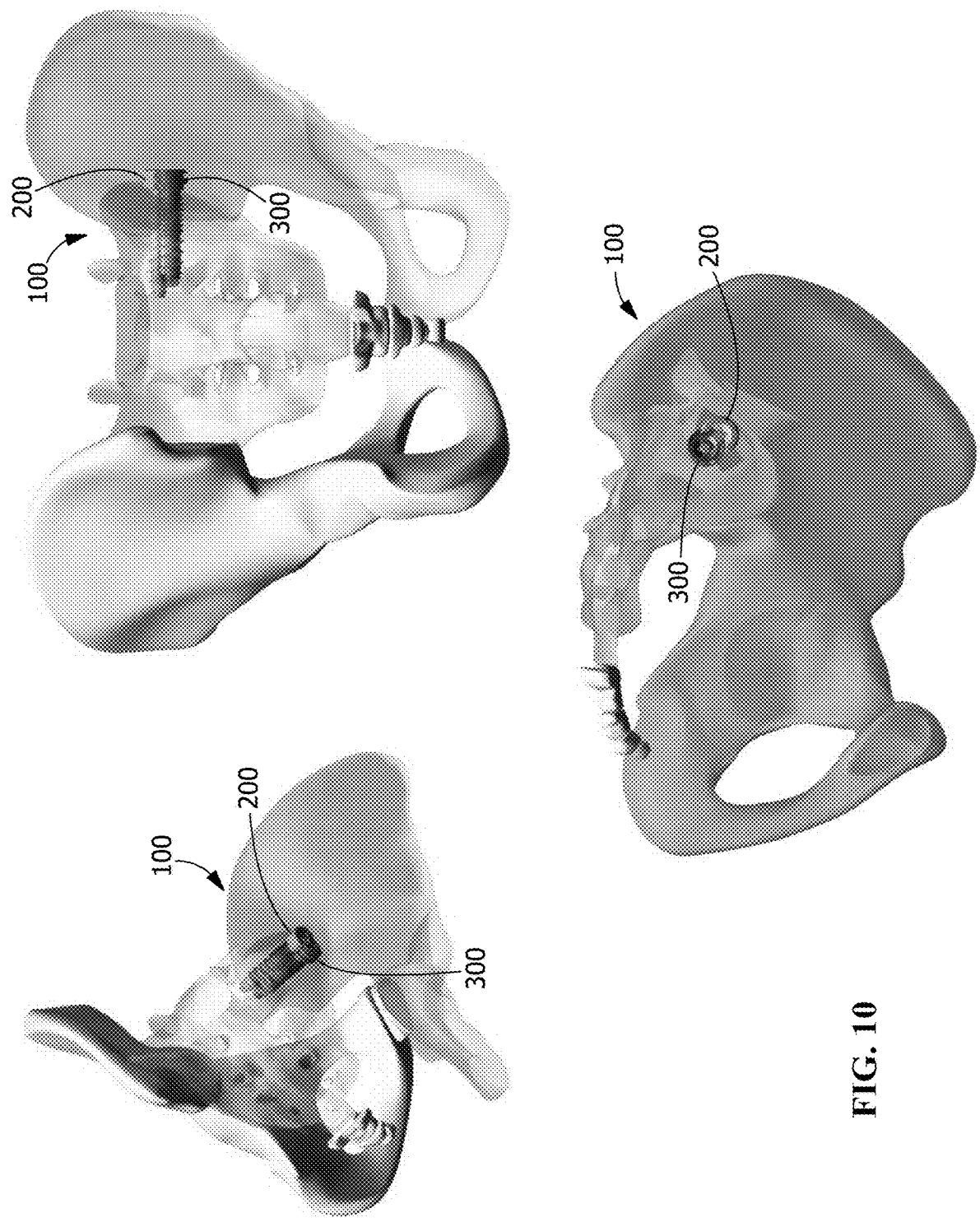

In some embodiments, only a single fixation implant is placed, the fixation implant selected from unitary fixation members and the dual fixation member implants disclosed herein. In some embodiments, a conventional drill guide or a drill guide as disclosed herein is used to select placement of at least a second fixation implant. In some embodiments, combinations of unitary implants and dual member fixation implants may be implanted. In some embodiments, a dual fixation member implant may be placed using a conventional drill guide, wherein the guide wires for each of the leading fixation member and the trailing fixation member are placed in series followed by placement in series of each of the leading and trailing fixation members, and in some embodiments, the guide wire followed by the leading fixation member are placed first, followed by the guide wire then the trailing fixation member. It will be appreciated that the distance between each of the guide wires, and/or the central axis of each of the fixation members when placed in the bone, will be determined by the head and elongate shank diameters of each of the fixation members, and will be influenced by the size and presence of elongate through-slots on the leading and optionally on the trailing fixation members. FIG. 10 shows lateral and oblique views of a representative image of a human pelvis, wherein a fixation implant is shown as implanted to join the sacrum and the ilium.

Fixation Implants: Dual Fixation Member Implants

Referring now to the drawings, FIG. 1 shows an exemplary embodiment of a fixation implant 100, where the leading and trailing fixation members 200, 300 each include a proximal head 110, a body 105 that includes an elongate shank 115 with a short and smooth shank portion and a longer threaded portion, and a distal tip 117, wherein one of the inter-engaging fixation members includes an elongate through-slot 120 through the head and a portion of the elongate shank 115, and each is cannulated 160 from the top 112 of the head through the distal tip 117. The depicted embodiment shows two fully cannulated 160 fixation members or screws that each have a head that includes complimentary dovetail threading 335 for inter-engagement, a short smooth shank portion and a continuously threaded portion with a variable thread profile, and a tapered threaded tip, wherein the leading fixation member 200 also includes an elongate through-slot 120. The leading fixation member 200 is adapted at its head with a proximal locking feature 230, 330 comprising female dovetails arranged in a spiral pattern characterized as cuts or notches 225 on the opposing edges of the elongate through-slot 120. The trailing fixation member 300 has corresponding male dovetail threads.

Figure 2A:
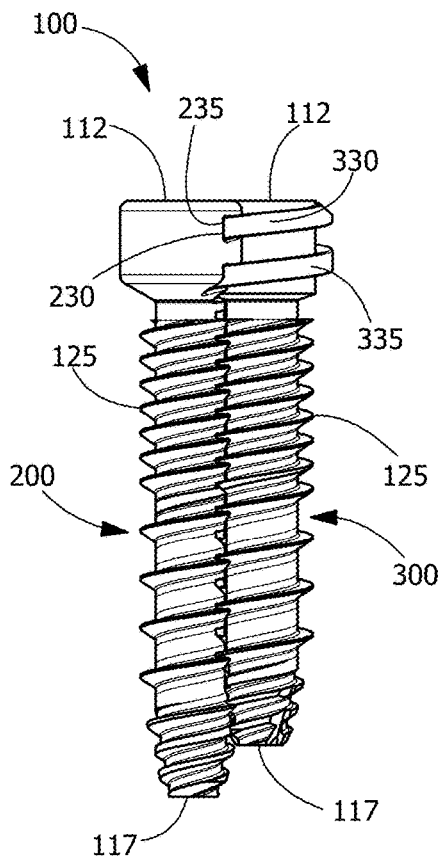
FIG. 2A shows the fixation implant fixation members as shown in FIG. 1 in a fully engaged configuration.
Figure 2B:
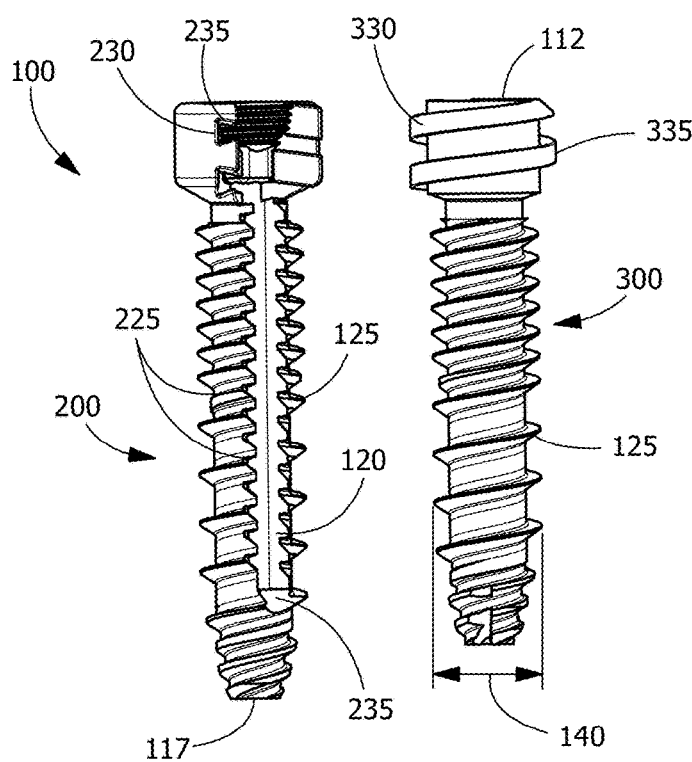
FIG. 2B shows the fixation implant fixation members as shown in FIG. 1 disassembled.
Figure 2C:
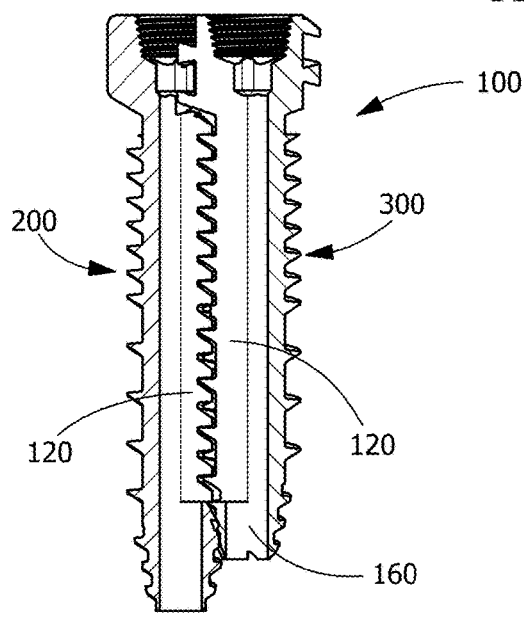
FIG. 2C shows a cross sectional view of the partially engaged fixation implant fixation members as shown in FIG. 1.
Figure 3A:
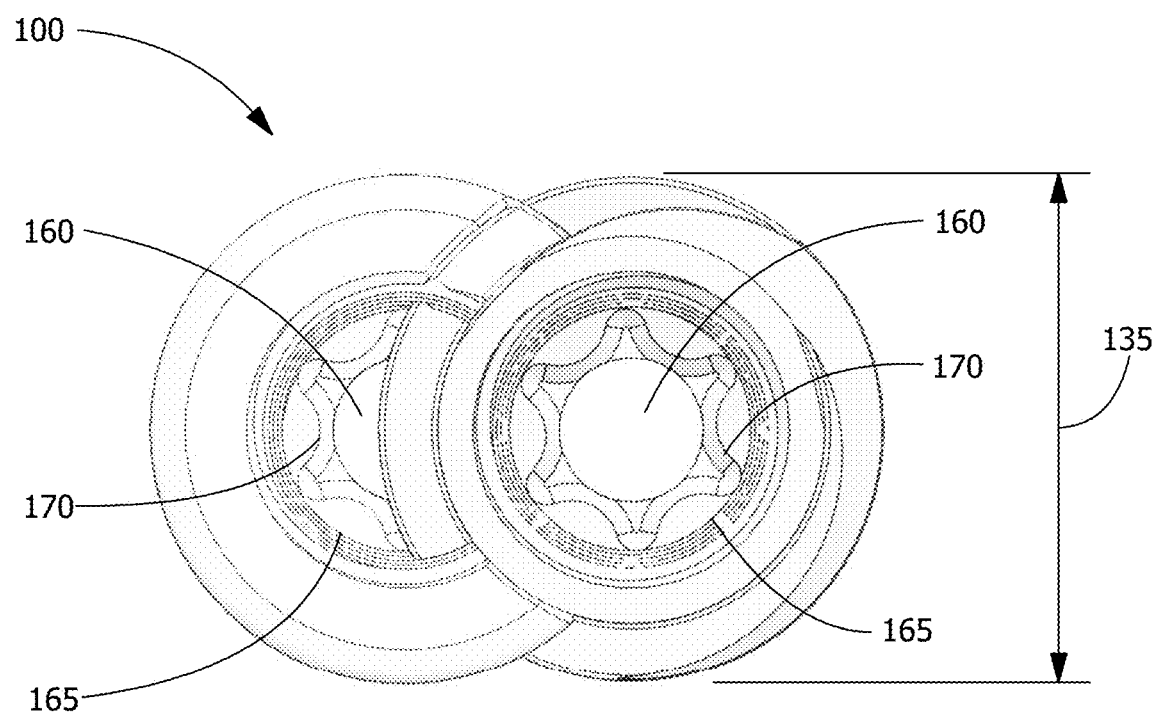
FIG. 3A shows a top plan view of the fully engaged fixation implant fixation members as shown in 2A.
Figure 3B:
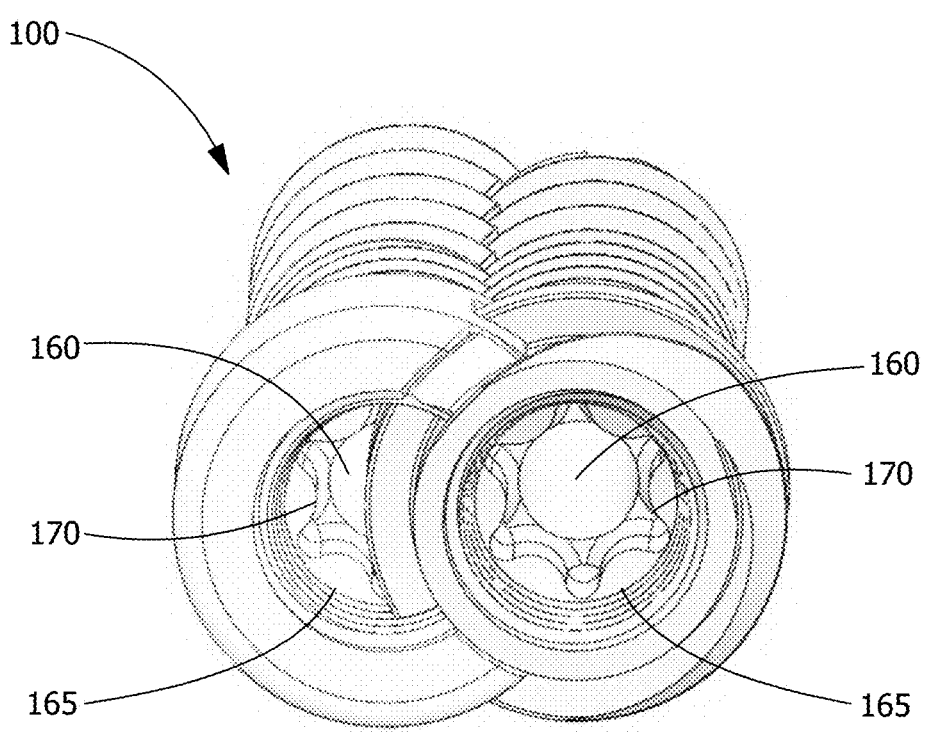
FIG. 3B shows a top perspective view of the fully engaged fixation implant fixation members as shown in FIG. 3A.
Figure 4A:
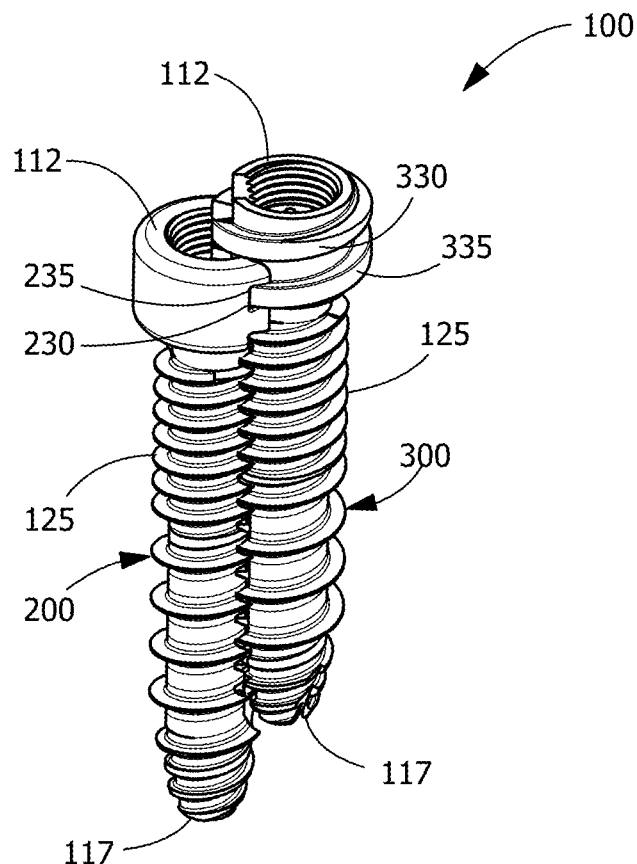
FIG. 4A shows another embodiment of a fixation implant that includes a pair of bone fixation members in a partially engaged configuration.
Figure 4B:
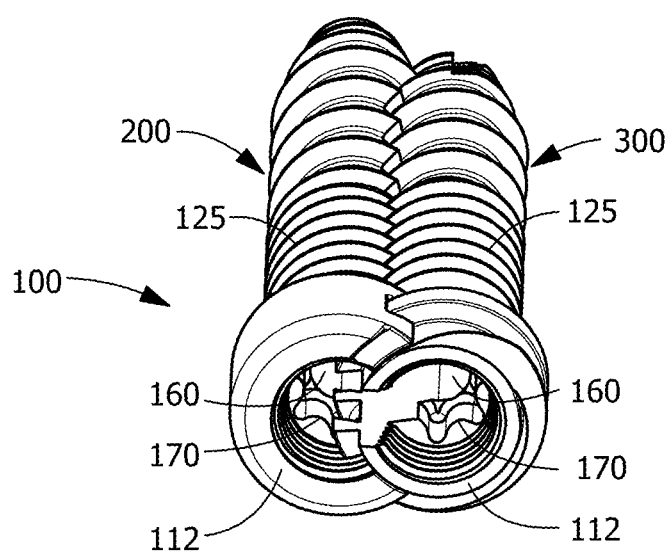
FIG. 4B shows the fixation implant fixation members as shown in FIG. 4A, fully engaged.

As shown in FIG. 2, when inter-engaged, the fixation members are eccentric, and the central cannula 160 of the fixation members forms a large space for the placement of bone graft and bone stimulatory materials, and further referring to FIG. 3, a side view of the engaged fixation members shows small openings along the length through which bony ingrowth can occur such that over time, the entire apparatus can achieve strong bony fixation. As can be seen from FIG. 2, the edges of the elongate through-slot 120 in each screw have partial notches 225 that are generally perpendicular to the center axis of the screw, the notches 225 enhancing interlacing of the edges of the screw when they are rotated together and providing flexion to enhance the engagement there between.

Referring again to FIG. 1, each of the pair of elongate fixation members has a body 105 that has a proximal head 110 and an elongate shank 115 and a center cannula 160. The body 105 has a length defined between a top 112 of the proximal head 110 and a distal tip 117 of the elongate shank 115. Each elongate shank 115 has a shape selected from generally cylindrical, generally conical, and generally frustoconical. And each head has a shape that is selected from generally spherical, generally hemispherical, generally cylindrical, generally conical, and generally frustoconical.

In accordance with the depicted embodiment, the leading fixation member 200 includes an elongate through-slot 120 along at least a portion of the length of the fixation member. In some exemplary embodiments, the elongate through-slot 120 has an origin at the top 112 the proximal head 110 and a base at a proximal portion of the distal tip 117 of the elongate shank 115. In the various embodiments, the leading fixation member 200 also includes notches 225 in opposing edges of the elongate through-slot 120, and a proximal locking feature 230, 330.

Figures 5A, 5B:
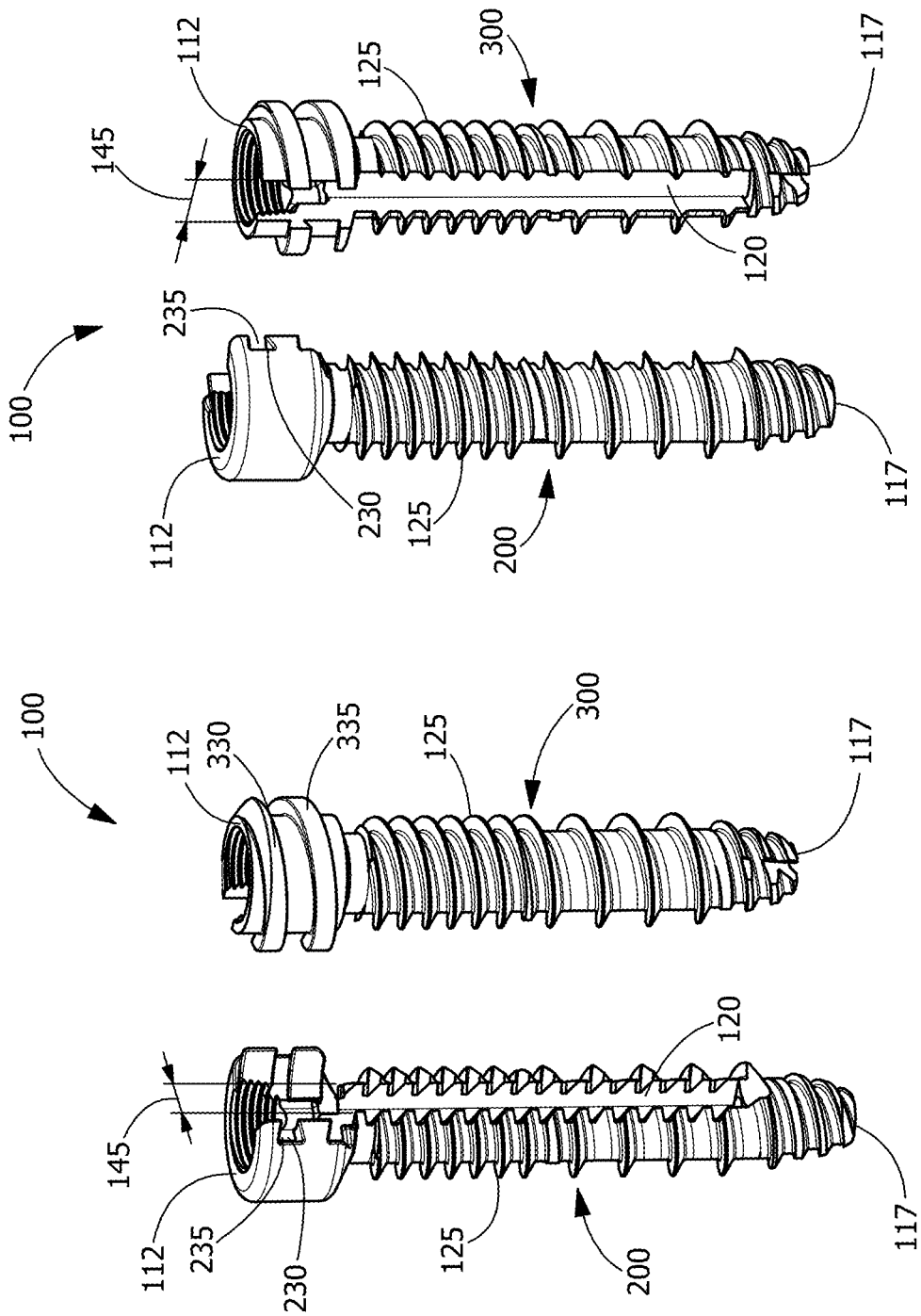
FIG. 5A shows a front view of disengaged fixation implant members as shown in FIG. 4.
FIG. 5B shows a back view of disengaged fixation implant members as shown in FIG. 5A.
Figure 6A:
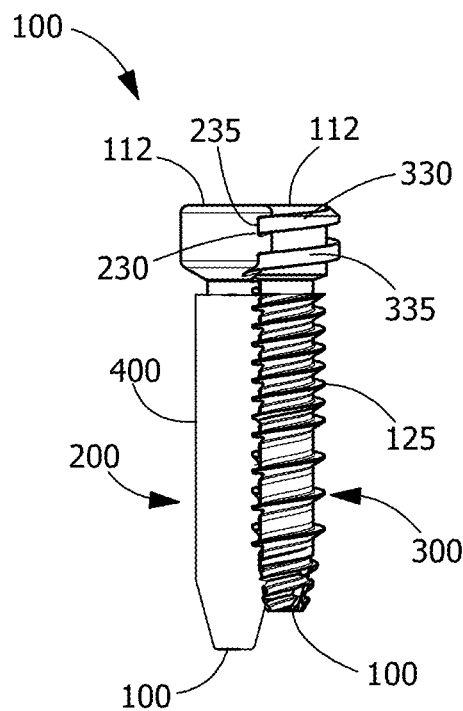
FIG. 6A shows yet another embodiment of a fixation implant according to the disclosure, the fixation members fully engaged.
Figure 6B:
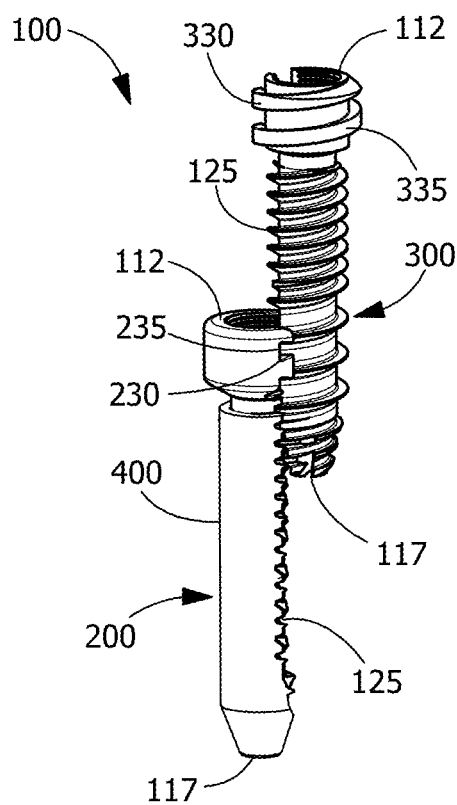
FIG. 6B shows the fixation implant as shown in FIG. 6A, the fixation members partially engaged.
Figure 6C:
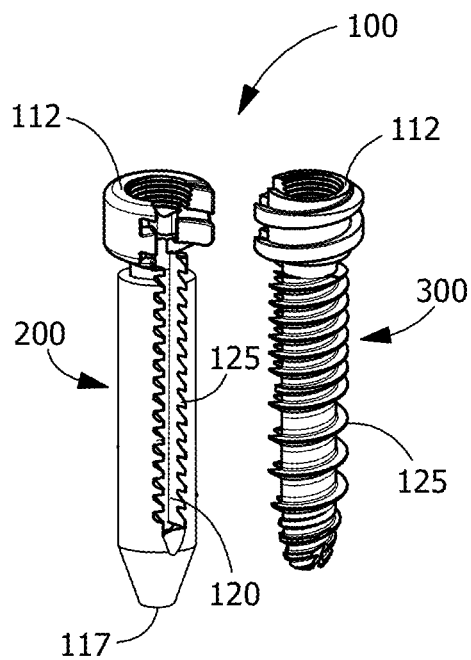
FIG. 6C shows the fixation implant as shown in FIG. 6A, the fixation members disengaged.
Figure 6D:
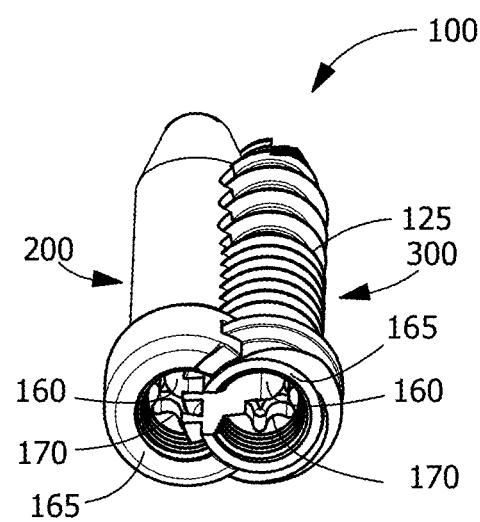
FIG. 6D shows top plan and top perspective views of the fully engaged fixation implant and fixation members as shown in FIG. 6A.
Figure 7A:
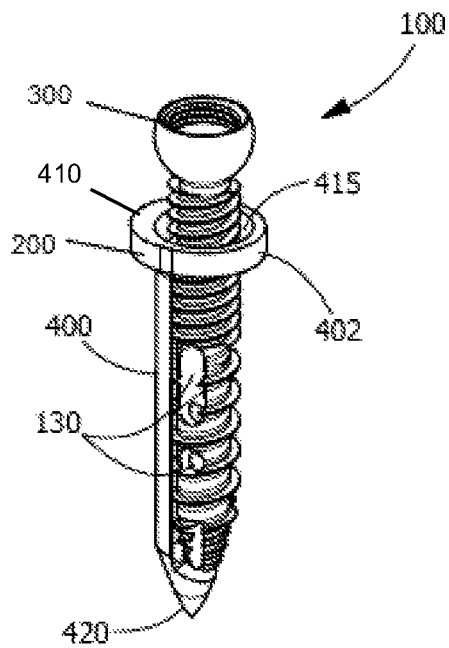
FIG. 7A shows yet another embodiment of a fixation implant according to the disclosure, the fixation members partially engaged.
Figure 7B:
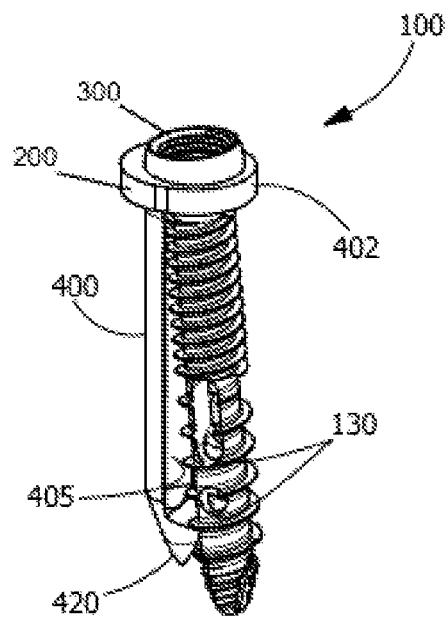
FIG. 7B shows the fixation implant as shown in FIG. 7A, the fixation members fully engaged.
Figure 7C:
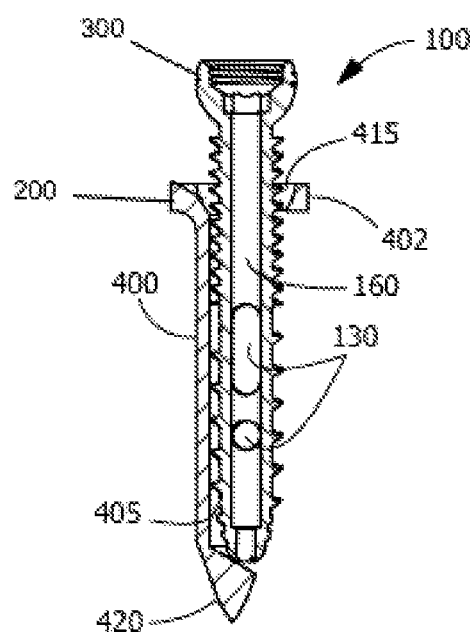
FIG. 7C shows a cross sectional view of the fixation implant shown in FIG. 7A.
Figure 7D:
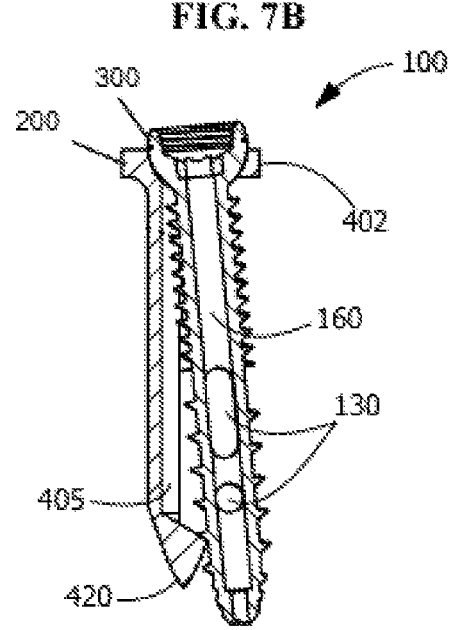
FIG. 7D shows a cross sectional view of the fixation implant shown in FIG. 7B.

Also in accordance with such embodiments, the trailing fixation member 300 optionally includes an elongate through-slot 120, one or more threads 125 arranged in a generally spiral pattern in relation to an outer circumference and along the length of the elongate shank 115, and a proximal locking feature 230, 330. In accordance with some embodiments, the trailing fixation member 300 includes an elongate through-slot 120 that extends from the top 112 of the proximal head 110 to a point that is proximal to the distal tip 117, as shown in FIG. 5.

In some alternate embodiments of the leading fixation member 200, the elongate through-slot 120 has an origin within but not at the top 112 of the proximal head 110 and a base at a point within the elongate shank 115 and above the tapered tip. In some specific embodiments, the elongate through-slot 120 has a base that is adjacent to a protruding ramp feature that is positioned below the slot and above the tapered tip, the ramp feature operable to contact a distal tip 117 of a trailing fixation member 300 and deflect the tip to distally splay the trailing fixation member 300 away from the leading fixation member 200. In yet other alternate embodiments of the leading fixation member 200, the shank is non-threaded and essentially smooth, as shown in FIG. 6.

Referring again to FIG. 1, the proximal locking feature 230 of the leading fixation member 200 comprises dovetail notches 225 arranged in a generally spiral pattern in relation to the outer circumference of its proximal head 110, and wherein the proximal locking feature 330 of the trailing fixation member 300 comprises one or more dovetail threads 335 arranged in a generally spiral pattern in relation to the outer circumference of its proximal head 110.

Referring now to FIG. 3, a top 112 view of the fixation implant 100 shows the interior of each of the fixation members, and the external thread profiles and dovetail engagement features. As shown, each proximal head 110 includes a top bore 165 and a tool engagement feature 170. As further described herein, the tool engagement feature is not limited to a hex shape as shown in the drawings, and may include any one or more features common to bone and other tissue screws. It will be appreciated that a suitable driver can be selected, including as needed a cannulated 160 driver.

In accordance with the various embodiments, the locking features of the heads may have another shape or configuration that is other than dovetailed. In some examples, the features may be squared, or trapezoidal shaped, or may include circular or elliptical shapes, or other shapes. And while the representative embodiments are shown with the male features on the trailing fixation member 300 and the female features on the leading fixation member 200, the placement of these may be switched or the engagement features may comprise combinations of male and female engagement features on one or the other of the heads of the fixation members. Further, in accordance with various embodiments, the dovetail proximal locking features 230, 330 of the fixation members have fit tolerances that are selected from tight and loose.

Figures 8A, 8B:
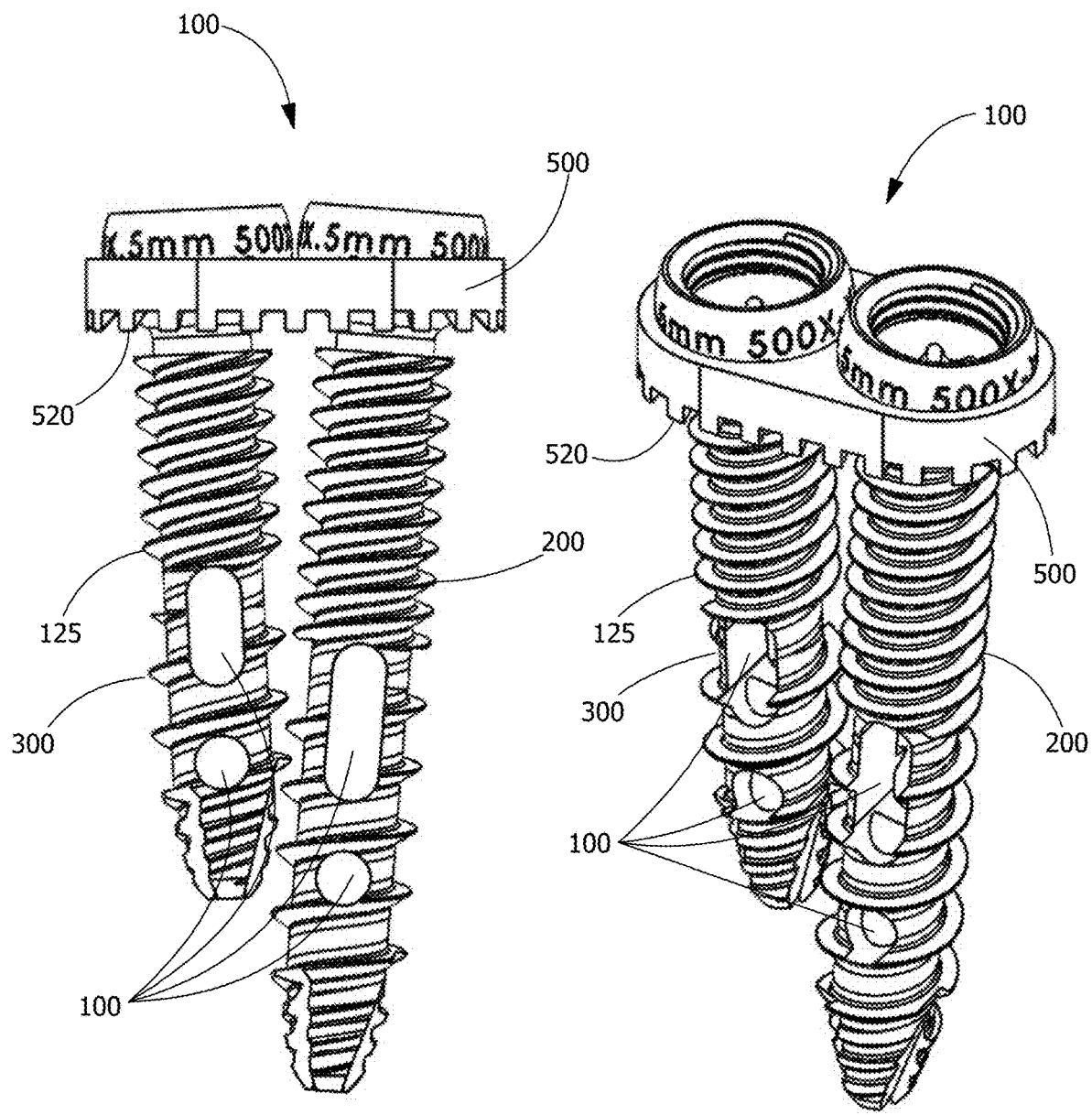
FIG. 8A shows yet another embodiment of a fixation implant according to the disclosure, the implant shown in side view, the fixation members and a fixation locking plate being fully engaged.
FIG. 8B shows the embodiment of a fixation implant shown in FIG. 8A in perspective view.
Figures 9A, 9B:
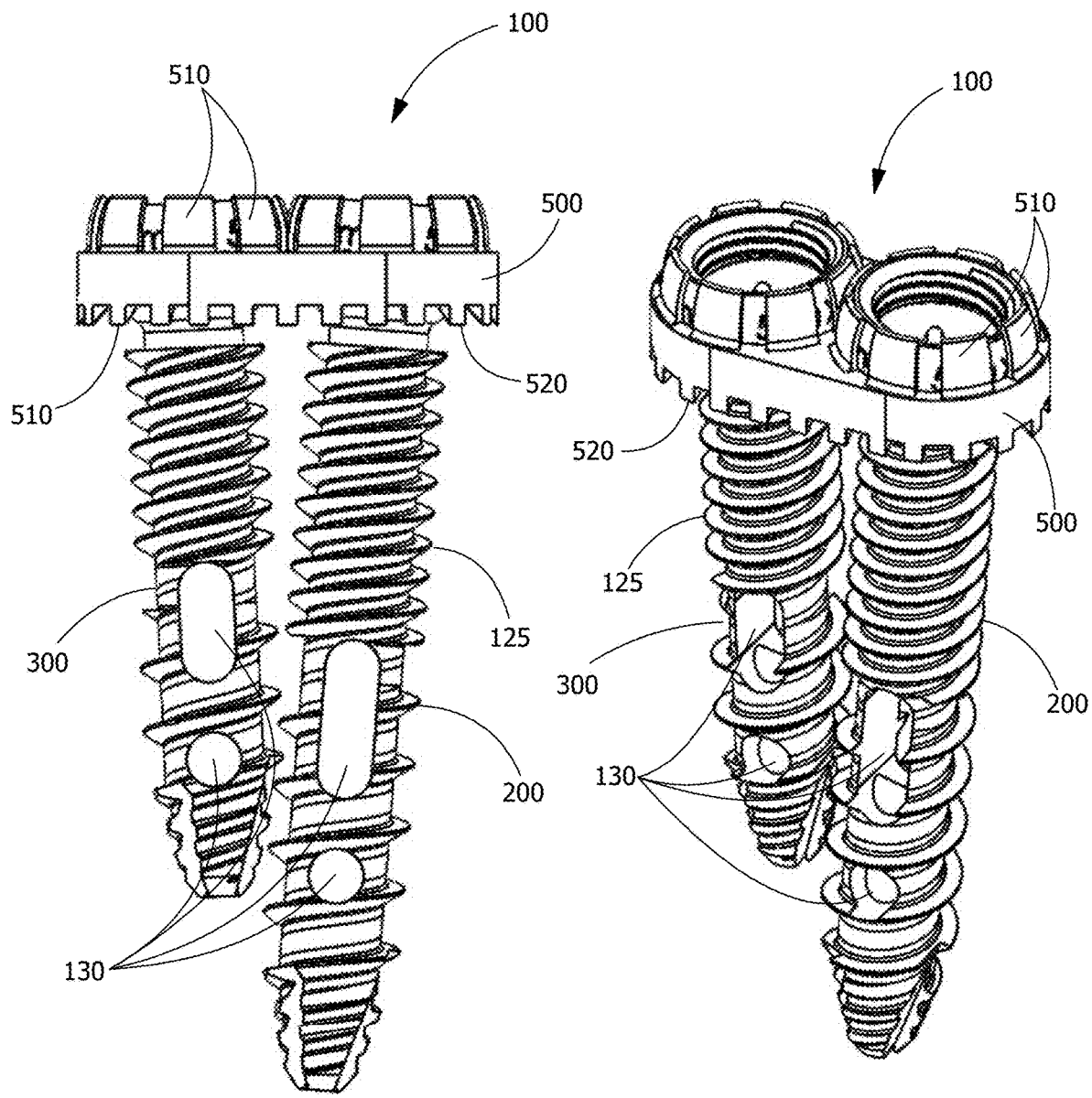
FIG. 9A shows yet another embodiment of a fixation implant according to the disclosure, the implant shown in side view, the fixation members and a fixation locking plate being fully engaged.
FIG. 9B shows the embodiment of a fixation implant shown in FIG. 9A in perspective view; and, FIG. 10 shows an embodiment of a fixation implant as shown in FIG. 1, the implant depicted as implanted in bone in the context of a representative human pelvic bone, the implant traversing the sacroiliac joint, depicted in anterior to posterior, lateral, and oblique views.

With further reference to FIG. 5, in accordance with some exemplary embodiments, the elongate through-slot 120 of each of the fixation members has an elongate through-slot 120 width 145 that is not greater than one half of a circumference of each of the proximal head 110 and the elongate shank 115 of the respective fixation members. And further according to some such embodiments, each of the fixation members has a slot width that is not greater than one third of a circumference 150, 155 of each of the proximal head 110 and the elongate shank 115 of the respective fixation members. In some embodiments, one or both of the pair of fixation members includes one or more short slot openings 130 in the elongate shank 115, as shown in the context of alternate embodiments in FIG. 7-FIG. 9.

Referring again to FIG. 2, in use, the fixation implant 100 are operable to be assembled by rotation of the trailing fixation member 300 adjacent to the leading fixation member 200, whereby cooperation between notches 225 in opposing edges of the elongate through-slot 120 and the threads 125 of the trailing member guide the engagement. Once fully contacted, the leading and trailing fixation members 300 may be releasably locked into engagement by cooperation of each of their respective proximal locking features 230, 330.

In use, the leading fixation member 200 may be driven into bone, for example, through the ilium, across the synovial joint adjacent to the sacrum, and into the sacrum. The trailing screw is then driven in adjacent to the first and upon the final turn are driven into engagement by intersection of the open notches 225 on one head with the male dovetail feature on the other head, whereby they are locked together. In some embodiments, the bone is first drilled with a pilot or larger hole prior to insertion of one or both screws. The pair of fixation members may be used in a variety of orthopedic applications for joint stabilization, fracture repair, plate fixation and stabilization, and the like.

In some other embodiments, the heads of the fixation members may be smooth and not adapted for inter-engagement, and the fixation implant 100 includes other features that encourage inter-engagement, such as for example, via engagement with one or more plates 500 or washers, as depicted in each of FIGS. 7A-7D, FIGS. 8A-8B and FIGS. 9A-9B.

As shown in FIGS. 7A-7D, an alternate embodiment of a fixation implant 100 is shown, the depicted embodiment, generally resembling a bone nail with a retaining ring at its proximal end and a taper at its distal end, is engageable as a leading fixation member 200 with a screw as a trailing fixation member 300. Referring now to the depicted embodiment of FIG. 7A, the fixation implant 100 includes the leading fixation member 200 having an elongate hemi-cylindrical shank 400 that includes a center axis, and a retaining head 402, wherein the retaining head 402 comprises a ring 410 with an eccentric aperture 415 (an aperture that is not concentric with the center axis of the shank), and wherein the hemi-cylindrical shank 400 comprises a center hollow 405 that forms the hemi-cylindrical shape and extends along at least a portion of the shank length from between the ring 410 and a tapered solid distal tip 420, and optionally, an expansion ramp 235 feature that is proximal to the distal tip 420. The trailing fixation member 300, as depicted, is a conventional bone screw.

In some embodiments, as shown in FIGS. 6A-6D, the trailing fixation member 300 is selected from a fixation member as described herein above, where such fixation member 100 has a body 105 that comprises a proximal head 110 and a elongate shank 115, the body 105 having a length defined between a top 112 of the proximal head 110 and a distal tip 117 of the elongate shank 115, and the elongate shank 115 having a shape selected from generally cylindrical, generally conical, and generally frustoconical, the body 105 further comprising (i) an optional elongate through-slot 120 along at least a portion of the length of the fixation member 10, the elongate through-slot 120 having an origin at the top 112 of or within the proximal head 110 and a base at the distal tip 117 of or within the elongate shank 115, (ii) optionally, at least one short slot in the shank, and (iii) a proximal locking feature 230 that is complimentary with the locking feature of the retaining head 402. When used, the fixation implant 100 is assembled by insertion of the trailing fixation member 300 into the eccentric aperture 415 of the proximal head 110 of the leading fixation member 200 and into engagement with the bone until the proximal locking features 230, 330 come into contact.

The leading and trailing fixation members 300 may be releasably locked into engagement by cooperation of each of their respective proximal locking features 230, 330. In some embodiments, contact between the distal tip 117 of the trailing fixation member 300 and an expansion ramp 235 feature of the leading fixation member 200 operates to splay apart the distal tips 117 of the fixation members when they are inter-engaged. In one example, the retaining head 402 ring 410 may include as a proximal locking feature 230 dovetail threads 335 arranged in a generally spiral pattern in an inner wall of the ring 410, and the trailing fixation member 300 may comprise dovetail notches 225 arranged in a generally spiral pattern in relation to the outer circumference of its proximal head 110 for locking engagement as described herein.

Referring again to FIG. 8 and FIG. 9, in accordance with yet other embodiments, the plates 500 or washers may include engagement features within the plate 500 for engagement with a corresponding engagement feature in a head of a fixation member. In other embodiments, such as shown in FIG. 9, the plate 500 or washer may include fingers or tabs that extend from the upper surface of the plate 500 and engage with the top 112 of a fixation member head via snap fit to retain a fixation head therein and prevent rotation or pullout. As depicted, the plate 500 or washer may include on a bone contact surface teeth or other bone engaging features 520 to secure the plate 500 or washer from slippage on the bone.

In one example, a tissue fixation implant 100 includes a pair of elongate fixation members each having a body 105 that comprises a proximal head 110 and a elongate shank 115, each fixation member having an elongate through-slot 120 along at least a portion of the length of the fixation member, and proximal locking feature 230, and a plate 500 that includes a bone contacting surface, a top 112 surface, a through aperture for receiving each of the fixation members and adapted to orient the fixation members in a convergent orientation, and a locking feature. s described herein, the plate 500 may have any of a variety of features generally known in the art including bone engagement features. In some embodiments, the plate 500 may have a single aperture, or two or more apertures, each aperture for receiving one or more fixation members or other conventional screws and plugs. In some embodiments, the plate 500 is adapted with a receiving seat in the aperture for cooperation with a base of the head to enable orientation of each screw in a convergent direction.

In one embodiment, a tissue fixation implant 100 includes a plate 500 with two apertures, each aperture shaped to receive the head of a fixation member. Each aperture has on an internal surface a locking feature that includes one or more dovetail threads 335 arranged in a generally spiral pattern around the inner periphery of the aperture. Each of the fixation members includes dovetail notches 225 arranged in a generally spiral pattern in relation to the outer circumference of its proximal head 110. Each of the leading and trailing fixation members 300 may be releasably locked into engagement by cooperation of each of their respective proximal locking features 230, 330 with the locking features of the plate 500.

In another embodiment, a tissue fixation implant 100 includes a plate 500 and two fixation members. The proximal locking features 230, 330 of each of the fixation members includes an array of detents in the head of the fixation member, and the locking feature of the plate 500 comprises an array of locking flanges 510 that extend from a periphery of the aperture which are adapted to snap fit with the detents to lock the fixation members to the plate 500. According to this example, the locking flanges 510 extend from the plate 500 so as to cover all or a portion of the periphery of the head. The array may include any number of two or more locking flanges 510 the number of which may be the same, or fewer than the number of receiving detents on the head of the fixation member. In some examples the locking flanges 510 are closely spaced while in others that are wide spaced. The locking flanges 510 splay upon insertion of the screw from the top 112 and when the screw head contacts the seat of the aperture, the locking flanges 510 snap and engage with the head detents. It will be appreciated that this is yet one example, and that other engagement features known in the art may be selected.

Further still, while in some embodiments, one or both of the fixation members are depicted in the drawings as cannulated 160, in some embodiments only a portion of one or both of the fixation members may be cannulated 160, and in some embodiments only one or neither fixation member is cannulated 160. Further still, in some embodiments, the fixation members may have the same diameters shared for each of the head, body 105 and tip.

Further still, in various embodiments, the fixation members may be adapted for engagement either in a generally parallel orientation, or in an orientation other than generally parallel. And in some embodiments, one or both fixation members may comprise one or more features along the body 105 length that upon contact between the fixation members cause one fixation member to skive away from the other fixation member and into engagement with the bone at an angle that diverges away from the other fixation member.

In yet further embodiments, the thread profile of either fixation member may be different from the other, and in some embodiments, each fixation member may be threaded but have a different threading profile. In some embodiments, only a portion of a fixation member is threaded, for example, in some such embodiments one fixation member may be threaded only at its tip, or at the head, or not at all, and in some embodiments a fixation member may be a plug. In some such embodiments, the shape of the fixation member may be other than circular in cross section across the elongate axis, and thus the fixation member may have any one of a non-circular shape including ovoid and triangular.

In some embodiments all or only a portion of a fixation member may be circular in cross section, and all or other portions of a fixation member may have a cross section that is other than circular, including ovoid and triangular. In some exemplary embodiments, a fixation member may have a frustoconical tip and a proximal adjacent portion that is triangular in cross section such that the tip can be pushed into a bone hole.

It will be appreciated by one of ordinary skill that while the fixation members depicted have certain features, other variations of the fixation members are possible. In particular, while the depicted embodiments shows fixation members having different lengths, where the leading fixation member 200 is shown as longer than the trailing fixation member 300, in some embodiments the lengths may be the same and in other embodiments one or the other may be longer. For example, in some embodiments one fixation member may be essentially a plug with one or more threaded or other engagement features and the other a fixation member having threading along a portion of or all of the body 105. And in another example, the fixation members may be short and have a wider or narrower diameter.

| References to the Drawings: Reference Numbers | |
| --- | --- |
| Fixation implant | 100 |
| Leading fixation member | 200 |
| Trailing fixation member | 300 |

| References to the Drawings: Reference Numbers | |
| --- | --- |
| Body | 105 |
| Proximal head | 110 |
| Elongate shank | 115 |
| Top | 112 |
| Distal tip | 117 |
| Elongate through-slot 120 | 120 |
| Notches | 225 |
| Proximal locking feature | 230, 330 |
| Expansion ramp | 235 |
| Threads | 125 |
| Short slot openings | 130 |
| Proximal head diameter | 135 |
| Elongate shank diameter | 140 |
| Elongate through-slot 120 width | 145 |
| Proximal head circumference | 150 |
| Elongate shank circumference | 155 |
| Cannula | 160 |
| Dovetail notches | 235 |
| Dovetail threads | 335 |
| Top bore | 165 |
| Internal engagement feature | 170 |
| Hemi-cylindrical shank | 400 |
| Center hollow | 405 |
| Retaining head | 402 |
| Ring | 410 |
| Eccentric aperture | 415 |
| Tapered solid distal tip | 420 |
| Plate | 500 |
| Locking flanges | 510 |
| Bone engaging feature | 520 |

While various inventive aspects, concepts and features of the general inventive concepts are described and illustrated herein in the context of various exemplary embodiments, these various aspects, concepts and features may be used in many alternative embodiments, either individually or in various combinations and sub-combinations thereof. Unless expressly excluded herein all such combinations and sub-combinations are intended to be within the scope of the general inventive concepts. Still further, while various alternative embodiments as to the various aspects, concepts and features of the inventions (such as alternative materials, structures, configurations, methods, devices and components, alternatives as to form, fit and function, and so on) may be described herein, such descriptions are not intended to be a complete or exhaustive list of available alternative embodiments, whether presently known or later developed.

Those skilled in the art may readily adopt one or more of the inventive aspects, concepts and features into additional embodiments and uses within the scope of the general inventive concepts, even if such embodiments are not expressly disclosed herein. Additionally, even though some features, concepts and aspects of the inventions may be described herein as being a preferred arrangement or method, such description is not intended to suggest that such feature is required or necessary unless expressly so stated. Still further, exemplary or representative values and ranges may be included to assist in understanding the present disclosure; however, such values and ranges are not to be construed in a limiting sense and are intended to be critical values or ranges only if so expressly stated.

Moreover, while various aspects, features and concepts may be expressly identified herein as being inventive or forming part of an invention, such identification is not intended to be exclusive, but rather there may be inventive aspects, concepts and features that are fully described herein without being expressly identified as such or as part of a specific invention. Descriptions of exemplary methods or processes are not limited to inclusion of all steps as being required in all cases, nor is the order that the steps are presented to be construed as required or necessary unless expressly so stated.

What is claimed is:

1. A tissue fixation implant, comprising:
   a leading fixation member having an elongate shank having a center axis, and a head, wherein the head comprises a ring with an open aperture that is not concentric with the center axis of the shank, wherein the elongate shank comprises a center hollow having a hemi-cylindrical shape and extending along at least a portion of a shank length from between the proximal ring and a tapered solid distal tip, and an expansion ramp feature that is proximal to the distal tip;
   a trailing fixation member having a body that comprises a proximal head and an elongate shank, the body having a length defined between a top of the proximal head and a distal tip of the elongate shank, and the elongate shank having a shape selected from generally cylindrical, generally conical, and generally frustoconical,
   wherein the tissue fixation implant is assembled by insertion of the trailing fixation member into the open aperture of a proximal head of the leading fixation member and into engagement with a bone,
   wherein the leading and trailing fixation members may be releasably locked into engagement by cooperation thereof, and
   wherein contact between the distal tip of the trailing fixation member and the expansion ramp feature of the leading fixation member operates to splay apart the distal tips of the fixation members when they are inter-engaged.

2. The tissue fixation implant according to claim 1, wherein the body of the trailing fixation member further comprising a central opening along at least the length of the fixation member, the central opening having an origin at the top of or within the proximal head and a base at the distal tip of or within the elongate shank.

3. The tissue fixation implant according to claim 1, wherein the body of the trailing fixation member further comprising at least one short slot in the shank.

* * * * *